United States Patent
Chlon et al.

(10) Patent No.: US 10,517,675 B2
(45) Date of Patent: *Dec. 31, 2019

(54) TREATMENT DEVICE FOR AREA AND LINE FRACTIONAL LASER TREATMENT

(71) Applicant: KONINKLIJKE PHILIPS N.V., Eindhoven (NL)

(72) Inventors: Caecilia Hendrina Theodora Chlon, Eindhoven (NL); Martin Jurna, Eindhoven (NL); Antonius Maarten Nuijs, Eindhoven (NL); Maria Angelina Josepha Rensen, Eindhoven (NL); Bastiaan Wilhelmus Maria Moeskops, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 800 days.

This patent is subject to a terminal disclaimer.

(21) Appl. No.: 14/907,696

(22) PCT Filed: Jul. 30, 2014

(86) PCT No.: PCT/EP2014/066367
§ 371 (c)(1),
(2) Date: Jan. 26, 2016

(87) PCT Pub. No.: WO2015/014889
PCT Pub. Date: Feb. 5, 2015

(65) Prior Publication Data
US 2016/0184017 A1 Jun. 30, 2016

(30) Foreign Application Priority Data

Jul. 30, 2013 (EP) .................... 13178444

(51) Int. Cl.
*A61B 5/06* (2006.01)
*A61B 18/20* (2006.01)
(Continued)

(52) U.S. Cl.
CPC .. *A61B 18/203* (2013.01); *A61B 2017/00876* (2013.01); *A61B 2018/0047* (2013.01);
(Continued)

(58) Field of Classification Search
CPC ........ A61B 18/203; A61B 2018/20359; A61B 2018/20351; A61B 2018/00876;
(Continued)

(56) References Cited

U.S. PATENT DOCUMENTS

2005/0143719 A1  6/2005 Sink
2009/0069741 A1* 3/2009 Altshuler ............... A61B 5/441
                                                        604/22
(Continued)

FOREIGN PATENT DOCUMENTS

GB    2486919 A   7/2012
WO    0071045 A1  11/2000

*Primary Examiner* — Aaron F Roane (57) ABSTRACT

The invention provides a treatment device (100) for fractional laser-based treatment. The treatment device comprises a treatment generator (80) comprising a treatment laser (20) and a laser scanning system (30). The laser scanning system comprises at least one movable deflection element and is configured and arranged for scanning laser light across an emission window (70) towards skin tissue (110) from a plurality of locations (74) in the emission window by moving the at least one deflection element relative to the emission window, whereby, in use, laser-based lesions (120) are generated inside the skin tissue. The treatment device also comprises a controller (60) for generating a predefined disposition of lesions (120) in the skin tissue by emitting laser light via selected ones of the plurality of locations in the emission window while the treatment device is moved (Continued)

relative to the skin surface (105). The controller is configured for generating an area disposition of the lesions by scanning the laser light across the emission window using the laser scanning system and deflecting laser light into the skin tissue via the plurality of locations while the treatment device is moved relative to the skin surface, whereas in the line treatment mode the controller is configured to generate a line disposition of the lesions inside the skin tissue from a single predefined location of the emission window by maintaining the at least one deflection element in a stationary position relative to the emission window while the treatment device is moved relative to the skin surface.

14 Claims, 6 Drawing Sheets

(51) Int. Cl.
*A61B 17/00* (2006.01)
*A61B 18/00* (2006.01)

(52) U.S. Cl.
CPC ............... *A61B 2018/00708* (2013.01); *A61B 2018/2025* (2013.01); *A61B 2018/2055* (2013.01)

(58) Field of Classification Search
CPC .. A61B 2018/00452; A61B 2018/0047; A61B 2018/00636; A61B 2018/00684; A61B 2018/00708; A61B 2018/2025
USPC .......................................................... 606/9
See application file for complete search history.

(56) References Cited

U.S. PATENT DOCUMENTS

2012/0197357 A1 8/2012 Dewey
2012/0283709 A1 11/2012 Reichert

* cited by examiner

TREATMENT DEVICE FOR AREA AND LINE FRACTIONAL LASER TREATMENT

This application is the U.S. National Phase application under 35 U.S.C. § 371 of International Application No. PCT/EP2014/066367, filed on Jul. 30, 2014, which claims the benefit of International Application No. 13178444.9 filed on Jul. 30, 2013. These applications are hereby incorporated by reference herein.

FIELD OF THE INVENTION

This invention relates to a treatment device for fractional laser-based skin treatment, the treatment device comprising:
an emission window,
a treatment generator comprising a treatment laser and a laser scanning system comprising at least one movable deflection element configured and arranged for scanning laser light across the emission window towards skin tissue from a plurality of locations in the emission window by moving the at least one deflection element relative to the emission window, whereby, in use, laser-based lesions are generated inside the skin tissue,
a controller configured for generating a predefined disposition of the lesions in the skin tissue by emitting laser light via selected ones of the locations while the treatment device, in use, is moved relative to the skin surface,
wherein the controller is configured for operating at least in an area treatment mode, and
wherein, in the area treatment mode, the controller is configured for generating an area disposition of the lesions inside the skin tissue by moving the at least one deflection element relative to the emission window while the treatment device, in use, is moved relative to the skin surface.

BACKGROUND OF THE INVENTION

The desire to maintain a youthful appearance by reducing wrinkles and fine lines in the skin is an important issue in human society. Many techniques have been designed to achieve the above issue, one of which is skin rejuvenation using, for example, fractional photo-thermolysis. This fractional photo-thermolysis may, for example, be used for treatment of lines, wrinkles, unevenness of pigmentation and dyschromia. Fractional photo-thermolysis is based on creating micro-zones of damage inside skin tissue within areas or volumes of unaffected skin tissue. The treatment either removes (ablative treatment) or thermally damages skin tissue in the micro-zones. The type of treatment, the density of the micro-zones and the depth of the micro-zones are chosen in relation to the skin treatment required and the type of skin to be treated.

A device for such fractional photo-thermolysis treatment is disclosed in US patent application US 2012/0197357. In this patent application, an apparatus, in particular a handheld apparatus, is disclosed for delivering optical energy. The apparatus includes an optical pattern generator inside the housing, which includes a rotatable component configured to continually rotate about a rotation axis in a single direction and to deflect the optical beam during rotation to divide the electromagnetic radiation into pulses that propagate from the housing toward the skin surface and form the fractional pattern at the skin surface.

The device as shown in the cited US patent application is typically used for an area treatment process in which the device employs means to scan one or more optical energy beams across a portion of tissue, and deliver the plurality of optical energy beams to a portion of tissue to be treated as the handheld apparatus is moved across the skin surface. Area treatment processes are often used to apply the fractional photo-thermolysis treatment over a specific area, for example, for treatment of unevenness of the skin tissue, and pigmentation and dischromia issues of the skin tissue. Alternatively, photo-thermolysis treatment may be desired as a line treatment process in which a user applies the treatment mainly across a wrinkle and/or a fine line. However, the known fractional photo-thermolysis apparatus is not configured for the line treatment process.

Consequently, a drawback of the known fractional photo-thermolysis apparatus is that it is not suitable or at least not optimal for the line treatment process.

OBJECT OF THE INVENTION

It is an object of the invention to provide a fractional laser based treatment device which may be used both for the area treatment process and the line treatment process.

SUMMARY OF THE INVENTION

In order to achieve this object, in accordance with the invention a treatment device for fractional laser-based treatment of the kind mentioned in the opening paragraph is characterized in that the controller is configured for operating alternatively in the area treatment mode and in a line treatment mode, wherein, in the line treatment mode, the controller is configured to generate a line disposition of the lesions inside the skin tissue by maintaining the at least one deflection element in a stationary position relative to the emission window while the treatment device, in use, is moved relative to the skin surface.

As mentioned before, area treatment processes are used to apply the treatment over a specific area, for example, for treatment of unevenness of the skin tissue, and pigmentation and dischromia issues of the skin tissue. For such area treatment to be time-effective, the treatment device comprises a laser scanning system comprising at least one movable deflection element to scan the laser light across the emission window for emitting the laser light from a plurality of locations towards the skin surface. The emission window may, for example, be an elongated area comprising a row or array of locations from which laser light may be emitted from the treatment device to treat multiple locations sequentially or simultaneously. To apply the area treatment process, the treatment device is moved generally in a main direction substantially perpendicular to a treatment axis which, for example, may be arranged substantially parallel to the row or array of locations in the elongated area of the emission window. However, when treating individual wrinkles and/or fine lines using such area treatment mode, much of the skin tissue around the wrinkle and/or fine line being treated may not necessarily require treatment and therefore may cause undesirable skin damage or skin reactions. Furthermore, the density of the lesions at or immediately around the wrinkle or fine line typically is too low in the area treatment mode compared to the requirements for an effective line treatment process. For that reason, with the treatment device according to the invention, a different line treatment process can be performed on wrinkles and/or fine lines, preferably with a higher local density of the lesions. To ensure that the treatment device according to the invention may be used both for the area treatment process and the line treatment process, the treatment device according to the invention is configured for maintaining the at least one deflection element in a stationary position relative to the emission window, such that the laser light is emitted from the emission window from a predefined fixed location during the line treatment. Thus, the treatment device according to the invention is configured to maintain the deflection element in the stationary position to generate the line disposition of lesions using a fixed location from which the laser light is emitted from the emission window. Using only this fixed location during the line treatment process enables the user to ensure that the light beams issuing from the emission window actually impinge on the wrinkle and/or fine line requiring treatment. Furthermore, a trigger to use only the fixed location in the emission window may, for example, also be used to adapt the lesion density generated by the treatment device according to the invention which, as mentioned before, typically is different for the line treatment process compared to the area treatment process. In addition to the improved positioning of the treatment device due to the use of this stationary position of the deflection element, causing the laser light to be emitted towards the emission window according to the invention, and in addition to the adapted local lesion density for the line treatment process, the use of such a fixed location in the emission window prevents the surroundings of the wrinkle and/or fine line from being treated as well. Therefore, the treatment device according to the invention is configured for applying both the area treatment process and the line treatment process.

In an embodiment of the treatment device, the laser scanning system comprises a rotatable deflection wheel having a plurality of deflection elements being configured for deflecting the laser light, during rotation of the deflection wheel, sequentially towards individual ones of the plurality of locations in the emission window. The treatment device is configured to operate the deflection wheel during the line treatment mode such that the position of the deflection wheel is stationary to ensure that the light is only emitted via a specific single one of the deflection elements of the deflection wheel to fix the location from which the laser light is emitted from the emission window. During the area treatment mode, the treatment device is configured to operate the deflection wheel such that substantially all deflection elements may be used. Such a deflection wheel may be a reflection wheel having reflection elements for reflecting laser light sequentially towards individual ones of the plurality of predefined locations. Alternatively, the deflection wheel may be a refraction wheel having refraction elements for refracting the laser light towards individual ones of the plurality of predefined locations.

In an embodiment of the treatment device, the deflection wheel is an axicon deflection wheel. The axicon deflection wheel is configured to substantially maintain the position of the laser light at the skin surface while the treatment device moves relative to the skin surface. This is achieved using a specific shape of the deflection element of the deflection wheel together with a specific rotation speed of the deflection wheel corresponding with the current motion of the treatment device relative to the skin surface. Furthermore, this maintaining of the position of the laser light spot may only be possible for a motion of the treatment device in a specific direction for example, in a direction substantially perpendicular to the treatment axis. A benefit of using such an axicon deflection wheel is that less laser power is required to generate the lesions inside the skin tissue as the laser light is more strongly focused inside the skin tissue.

In an embodiment of the treatment device, the controller is configured for generating the line disposition of the lesions inside the skin tissue by maintaining the rotatable deflection wheel in a stationary angular position relative to the emission window. Preventing the deflection wheel from rotating is a relatively cost-effective way of selecting the fixed location of the light emitted from the emission window. Preferably, the position of the deflection wheel, while in a fixed position, is known, such that indeed the laser light is emitted via the specific one of the number of predefined locations from the emission window.

In an embodiment of the treatment device, the deflection wheel, in the line treatment mode, is maintained in the stationary angular position relative to the emission window by means of a blocking mechanism. Said blocking mechanism may comprise a mechanical blocking element for mechanically preventing the deflection wheel from rotating. Alternatively, the blocking mechanism may comprise a magnetic blocking element for magnetically preventing the deflection wheel from rotating. Even further alternatively, the blocking mechanism may comprise an electrical blocking mechanism for interrupting a supply of power to a motor configured for rotating the deflection wheel.

In an embodiment of the treatment device, the blocking mechanism is configured for blocking the deflection wheel in a predefined stationary angular position relative to the emission window, wherein the laser light is deflected towards a predefined one of the plurality of locations in the emission window. When the deflection wheel is blocked in the predefined stationary angular position, the laser light will be emitted from the predefined one of the plurality of locations in the emission window.

In an embodiment of the treatment device, the blocking mechanism, when maintaining the deflection wheel in the stationary angular position relative to the emission window, generates a signal indicating to the controller that the deflection wheel is in a blocked condition. This signal may be used to trigger the controller to apply the line treatment mode in which the laser light modulation is used for generating the predefined disposition of lesions while the treatment device moves relative to the skin surface.

In an embodiment of the treatment device, the treatment device comprises a guidance element for indicating to a user a predefined location in the emission window from which, in the line treatment mode, the laser light is emitted towards the skin tissue. Such a guidance element indicates where the laser light is emitted during the line treatment mode and hence such a guidance element may assist in ensuring that the lesions are generated at the correct location inside the skin tissue.

In an embodiment of the treatment device, the guidance element comprises a protruding part protruding from a part of a housing of the treatment device surrounding the emission window. Such a protruding part provides a tangible guidance element for identifying where, in use, the laser light is emitted from the emission window. This protruding part may be "tip"-shaped, said tip having dimensions allowing it to easily treat wrinkles or fine lines on the skin surface.

In an embodiment of the treatment device, the guidance element comprises a visible indicator. Optionally, the visible indicator comprises an optical projection of an indicator on the skin surface near the emission window using visible light. Such a projection may be done using, for example, a low-power laser light source, such as a laser diode. Optionally, the visible indicator comprises an optical projection of an indicator on a part of a housing of the treatment device surrounding the emission window using visible light. Also here the visible indicator may be generated using a low-power laser light source. Alternatively, the visible indicator may comprise a light emitting indicator attached to the treatment device near the emission window. Still further optionally, the visible indicator may comprise a colored marker applied on a part of a housing of the treatment device surrounding the emission window.

In an embodiment of the treatment device, the treatment device has an intended movement direction in which, at least in the line treatment mode, the treatment device is to be moved relative to the skin surface, and wherein the guidance element comprises a mechanical guidance element which comprises an extension protruding parallel to the intended movement direction from a part of a housing of the treatment device surrounding the emission window. Such an extension may have any shape for identifying where, in use, the laser light is emitted from the emission window, such as a triangular shape or even a shape similar to an arrow tip. Alternatively, the mechanical guidance element may comprise a rolling element attached to a part of a housing of the treatment device surrounding the emission window and configured for rolling, in use, over the skin surface for indicating a location from where the laser light is emitted from the emission window during the line treatment mode. Such a rolling element may be a wheel, for example, rotating in a rotation plane. The rolling element is arranged such that its rotation plane intersects with a center of the predefined location in the emission window from which the laser light, in use, is emitted during the line treatment mode.

In an embodiment of the treatment device, the guidance element comprises a mechanical guidance element comprising two extensions arranged adjacent to each other and configured for, in use, contacting the skin surface, said two extensions protruding from a part of a housing of the treatment device surrounding the emission window and converging towards each other in a direction away from the emission window. Preferably, the opening between the two adjacent extensions forms a kind of triangular opening in which the two adjacent extensions do not touch too close to the opening. Therefore, when the mechanical guidance element slides across the skin surface, the opening at the top of the triangle guides the part of the skin which has to be treated towards the predefined location in the emission window from which the laser light is emitted. Due to the triangular shape, the guided skin part will be stretched which ensures good contact between the predefined location of the emission window from which the laser light is emitted during the line treatment mode and the skin. In an embodiment, the mechanical guidance element comprises two rolling elements arranged adjacent each other and configured for, in use, rolling over the skin surface, wherein an intermediate space between said two rolling elements converges in a direction away from the emission window. Also such adjacent rolling elements, which may form a kind of triangular arrangement, preferably do not touch, so that the triangular shape of the opening on the side facing away from the emission window is preferably open to guide the part of the skin which will be treated towards the predefined location in the emission window from which the laser light is emitted. This triangular arrangement of the adjacent rolling elements subsequently stretches the guided part of the skin to ensure good contact between the emission window and the skin surface.

In an embodiment of the treatment device, the treatment device is a handheld treatment device. Such a handheld treatment device may be operated using batteries or may be connected to electric power via a power cord.

These and other aspects of the invention are apparent from and will be elucidated with reference to the embodiments described hereinafter.

DETAILED DESCRIPTION OF THE INVENTION

Figure 1:
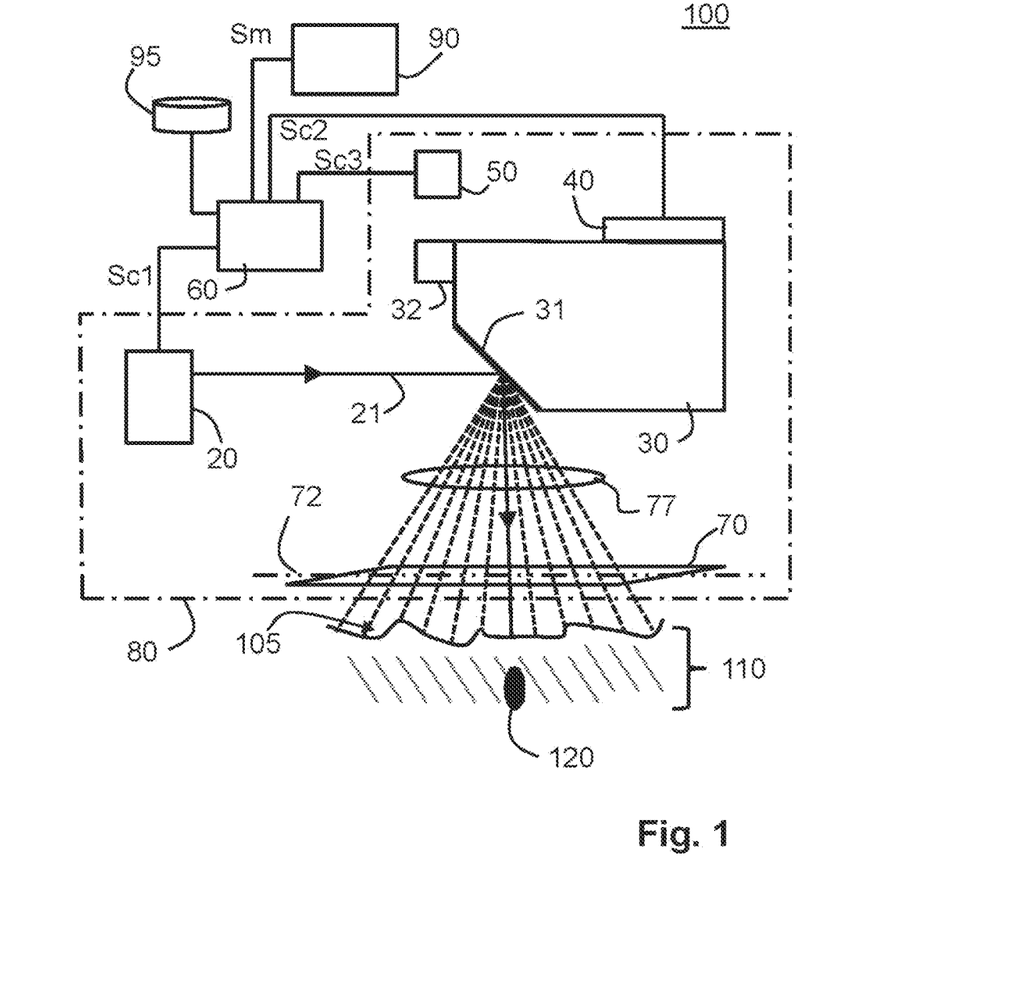
FIG. 1 schematically shows a treatment device according to the invention.

FIG. 1 schematically shows a treatment device 100 according to the invention. The treatment device 100 comprises a treatment laser 20 for providing a light beam 21. A deflection wheel 30 comprises a plurality of deflection elements 31 which deflect the light beam 21 through an objective lens 77 and an emission window 70 of the treatment device 100 towards skin tissue 110. Each deflection element 31 provides a respective different direction of reflection for the light beam 21, causing the reflected light beam 21 to be emitted from the treatment device 100 via different predefined locations 74 (see FIGS. 3A, 3B and 3C). Accordingly, during rotation of the deflection wheel 30, the light beam 21 is reflected via the plurality of different predefined locations 74 in the emission window 70 towards a corresponding plurality of different locations at the skin surface 105. At the skin surface 105, the light beams enter the skin tissue 110 and create lesions 120 inside the skin tissue 110. Lesions 120 are also known as microscopic treatment zones (MTZs) of thermally denatured skin tissue 110 and the fractional application of lesions 120 creates a predefined disposition of lesions 120 inside the skin tissue 110, surrounded by unaffected skin tissue 110. This treatment activates the skin repair mechanisms and improves skin appearance. The treatment laser 20 is coupled to a control circuit 60 which controls the treatment laser 20 to illuminate individual deflection facets 31 at selected moments. The deflection wheel 30 is rotated by driving means 40, such that the different deflection facets 31 of the deflection wheel 30 successively cross the path of the incoming light beam 21. In the embodiment shown in FIG. 1, the deflection facets 31 constitute reflective facets 31 whose reflective surfaces are oriented at different angles with respect to the incoming light beam 21 in order to reflect the light beam 21 towards different predefined locations 74 in the emission window 70 to impinge on the skin surface 105 at different locations. Alternatively, the deflection wheel 30 may comprise a refractive element (not shown) for refracting (not shown) the incoming light beam 21 towards the different predefined locations 74 of the emission window 70. Still further alternatively, the deflection wheel 30 may comprise an axicon deflection wheel (not shown) whose reflective or refractive surfaces are shaped such that the spot created by the light beam 21 on the skin surface 105 remains substantially static while the treatment device 100 is being moved relative to the skin surface 105. Such axicon deflection wheels are known in the art and the rotation speed of these axicon deflection wheels has to relate to the motion of the treatment device 100 relative to the skin surface 105 to ensure that the spot remains substantially static.

The deflection wheel 30 as shown in FIG. 1 (and also FIGS. 2A and 2B) further comprises triggering flakes 32 which are provided next to the deflection facets 31. The passage of triggering flakes 32 is detected by a flake detector 50. The flake detector 50 is coupled to the control circuit 60. The frequency of the trigger signal generated by the flake detector 50 determines the rotational speed signal Sc2 of the deflection wheel 30. In addition, the control circuit 60 controls a modulation of the light beam 21 based on the trigger signal to select through which of the plurality of predefined locations 74 (see FIGS. 3A, 3B and 3C) the treatment light is emitted during the treatment.

The deflection wheel 30 may, for example, comprise twelve deflection facets 31, and the control circuit 60 may, for example, modulate the light beam 21 to provide a light pulse at 2, 4, 6 or even 12 of the deflection facets 31 passing during one rotation. This modulation of the light beam 21 may be used to determine a density of the disposition of lesions 120 inside the skin tissue 110 during the treatment. Furthermore, the device 100 comprises a motion sensor 90 for determining motion of the treatment device 100 relative to the skin surface 105—also further indicated as "hand speed" being the speed with which a user drags the treatment device 100 along the skin surface 105. The control circuit 60 is configured to adapt the modulation of the light beam 21 (for example, via controlling an on/off switching of the light source 20) depending on the measured motion (or hand speed) in order to provide the predefined disposition of lesions 120 (or MTZs) at a more or less constant density being substantially independent of the motion (or hand speed).

In addition to the controlling of the modulation of the light beam 21, the controller 60 may further be configured to select the actual deflection facets 31 via which the light beam 21 is deflected towards the skin surface 105—and hence to control the actual predefined location 74 via which the light is emitted from the treatment device 100 into the skin tissue 110. To achieve this, the flake detector 50 of treatment device 100 may, for example, receive a specific reply signal from a predefined flake 32 of the plurality of flakes 32, which enables the controller 60 to identify the position of that predefined flake 32—and hence identify a position of a predefined one of the deflection facets 31 and a predefined one of the predefined locations 74 in the emission window 70. When the position of the remainder of the deflection facets 31 is known to the controller 60, the controller 60 may, for example, use the modulation of the light beam 21 to define which of the deflection facets 31 should be used to emit the next light beam 21 towards the skin surface 105 to generate the lesion 120 inside the skin tissue 110. The controller 60 may also control a power Sc1 of the treatment laser 20 and, for example, a focusing depth of the treatment laser 20 to enable the severity of the laser-based fractional treatment to be varied.

The treatment device 100 according to the invention further comprises a storage device 95 for storing information related to the required modulation of the light beam 21, the required rotation speed of the deflection wheel 30 and other parameters relevant to generate the predefined disposition of the lesions 120 inside the skin tissue 110. Such information may, for example, be stored on the storage device 95 in Look-Up tables from which the controller 60 can retrieve the required information depending on, for example, the sensed motion Sm. The motion sensor 90 may be able to sense a speed of the sensed motion Sm and a direction of the sensed motion Sm. Using these Look-Up tables, the controller 60 may find specific modulation requirements of the light beam 21 and specific timing requirements to ensure that the correct deflection facet 31 is used to generate the predefined disposition of lesions 120 inside the skin tissue 110.

Figure 2A:
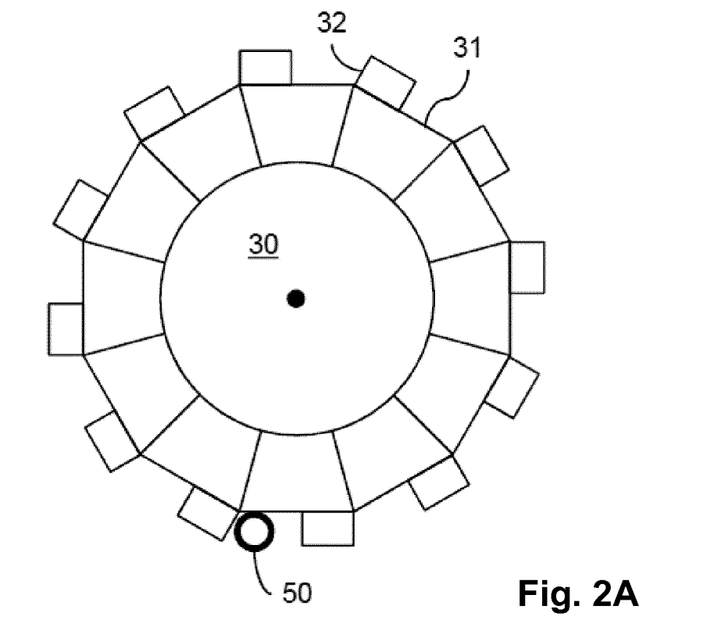
FIGS. 2A and 2B schematically show different views of a deflection wheel of the treatment generator, FIGS. 3A, 3B and 3C schematically show arrangements of predefined locations in the emission window of the treatment device.
Figure 2B:
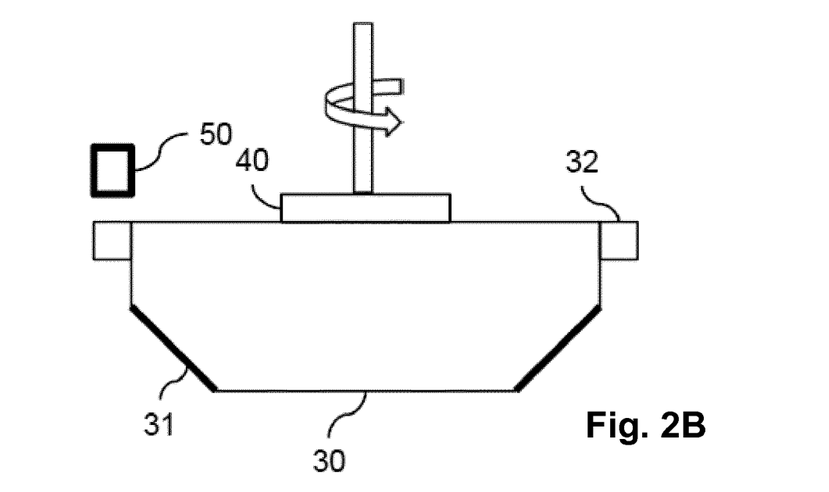

FIGS. 2A and 2B schematically show different views of a deflection wheel 30 of the treatment generator 80, in which the deflection wheel 30 is a reflection wheel 30. FIG. 2A shows a possible location of the flakes 32 relative to the flake detector 50 and FIG. 2B shows a possible embodiment of the deflection facets 31 being reflection facets 31. It will be apparent to the person skilled in the art that many variations to such a deflection wheel 30 may be possible. Also, the reflection facets 31 shown in FIGS. 2A and 2B are substantially flat, while in an alternative embodiment the reflection wheel 30 may be an axicon deflection wheel (not shown) whose deflection facets are curved such that the light beam 21 reflected from these deflection facets remains substantially at the same location on the skin surface 105 during the deflection from that facet. A benefit of such an arrangement is that the lesions 120 are not elongated due to the moving of the treatment device 100 and therefore less light energy is required to efficiently generate lesions 120 inside the skin tissue.

Figure 3A:
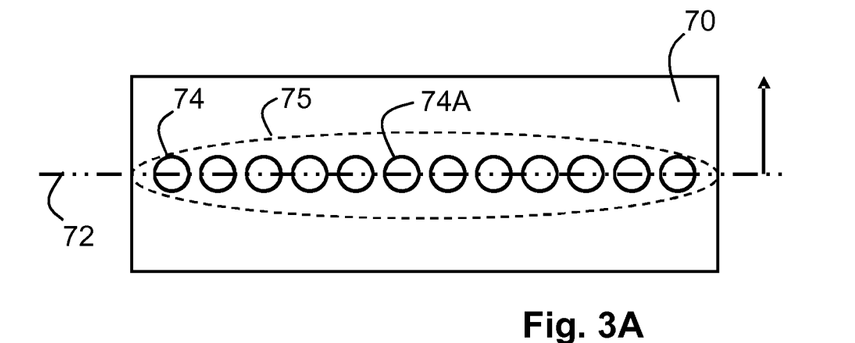
Figure 3B:
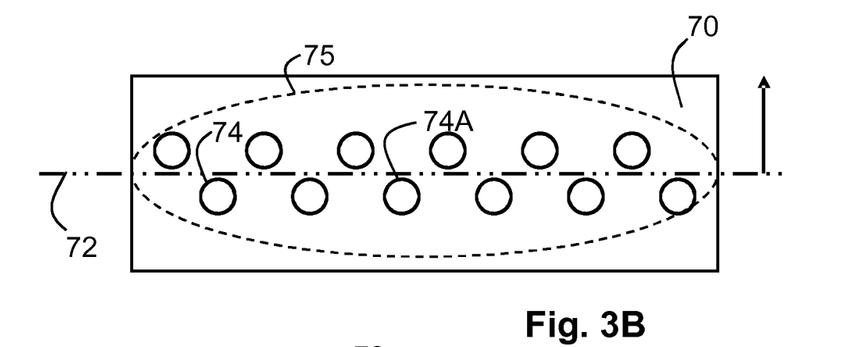
Figure 3C:
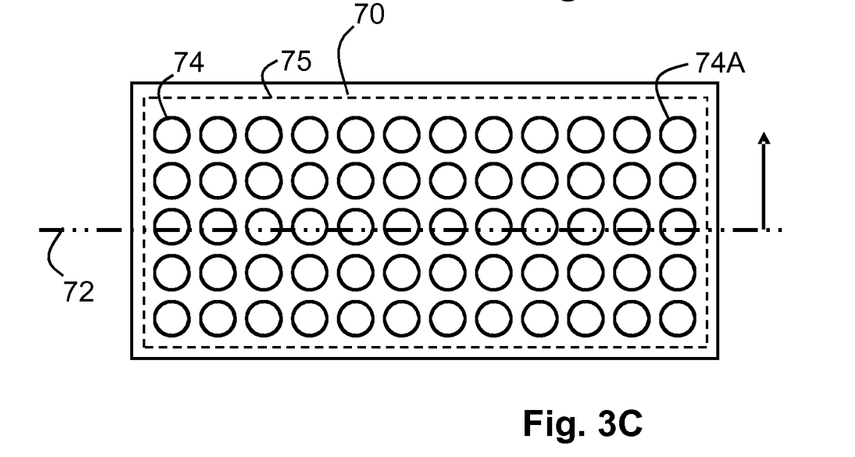

FIGS. 3A, 3B and 3C schematically show arrangements of predefined locations 74 in the emission window 70 of the treatment device 100. Each of these arrangements of predefined locations 74 may be produced by the treatment generator 80 shown in FIG. 1. For example, FIG. 3A shows an arrangement of predefined locations 74 which are disposed on the treatment axis 72 within an elongated area 75. FIG. 3B shows an arrangement of predefined locations 74 which are disposed on either side of the treatment axis 72 within the elongated area 75 in the emission window 70. FIG. 3C shows a two-dimensional array of predefined locations 74 distributed across the emission window 70. The treatment device 100 according to the invention is configured to use only a single one 74A (also further indicated as the specific one 74A) of the predefined locations 74 during the line treatment mode due to the stationary position of the at least one deflection element relative to the emission window during the line treatment mode, while the treatment device 10 is further configured to use substantially all available predefined locations 74 during the area treatment mode. In FIGS. 3A and 3B, the specific one 74A is located substantially in the center of the emission window 70, while in FIG. 3C the specific one 74A is located at the edge of the two-dimensional array of predefined locations 74. A benefit of using a single one 74A for generating the line treatment process is that only very limited safety measures are required for preventing that two lesions are generated too close to each other.

Figure 4A:
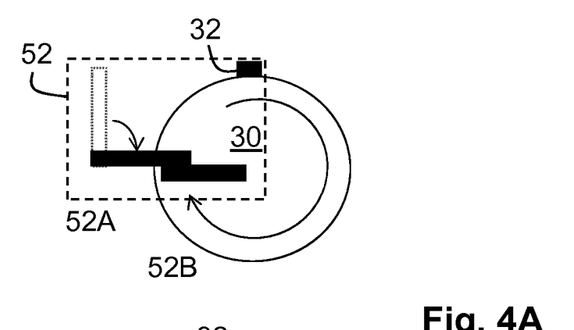
FIGS. 4A, 4B and 4C show different blocking mechanisms for blocking the deflection wheel.
Figure 4B:
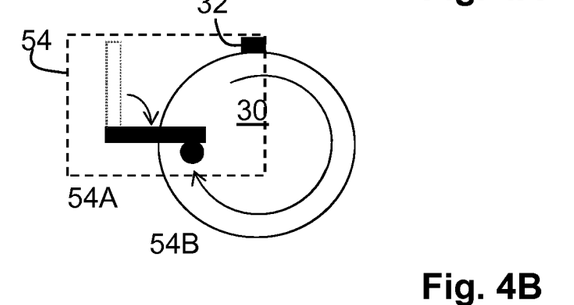
Figure 4C:
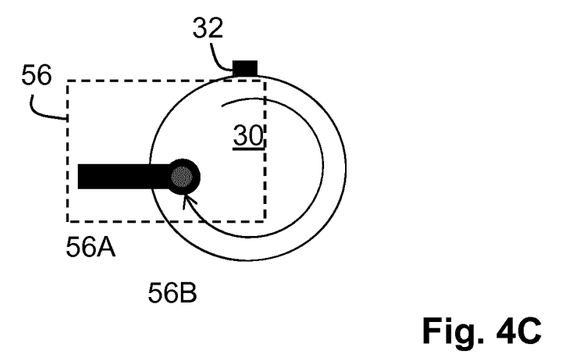

FIGS. 4A, 4B and 4C schematically show different blocking mechanisms 52, 54, 56, respectively, for blocking the deflection wheel 30 and to ensure that the at least one deflection element 31 is in a stationary position relative to the emission window 70. Only part of the deflection wheel 30 is shown, including one of the flakes 32, while the deflection elements (indicated with reference number 31 in FIG. 1) are omitted. The blocking mechanism 52, 54, 56 may comprise a switch 52A, 54A, which may be rotated by a user (indicated with the curved arrow) to engage with a rod 52B or a knob 54B for maintaining the deflection wheel 30 in a stationary angular position relative to the emission window 70. In FIG. 4C, the blocking mechanism 52, 54, 56 comprises a switch 56A which, for example, comprises an electro-magnet 56A which is configured to engage with a metal knob 56B such that the angular position of the deflection wheel 30 is fixed. Finally, the blocking mechanism may be an electrical blocking mechanism (not shown) which is controlled by the controller 60 and which may, for example, fix the angular position of the deflection wheel 30 relative to the emission window 70 by interrupting a supply of power to the motor 40 of the deflection wheel 30. Such blocking mechanisms 52, 54, 56 may be used to fix the angular position of the deflection wheel 30 such that a specific deflection element (not indicated) is used to deflect the laser light 21 to be emitted via the specific one 74A (see FIG. 3A) of the plurality of predefined locations 74. Of course also combinations of such blocking mechanisms may be used by the treatment device 100, such as a combination of a mechanical blocking mechanism which subsequently activates the electrical blocking mechanism, or a magnetic blocking mechanism which subsequently activates the electrical blocking mechanism. The blocking mechanism 52, 54, 56 according to the invention may also comprise a switch (not shown) or some kind of trigger (not shown) to indicate to the controller 60 that the blocking mechanism is active. Subsequently, the controller may automatically switch to the line treatment mode of operation.

Figure 5A:
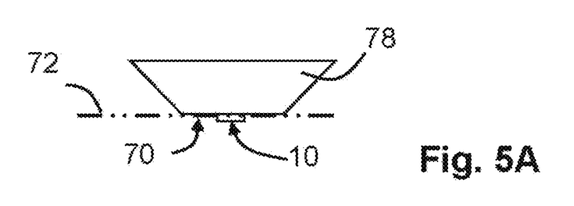
FIGS. 5A, 5B, 5C, 5D and 5E show different guidance elements.
Figure 5B:
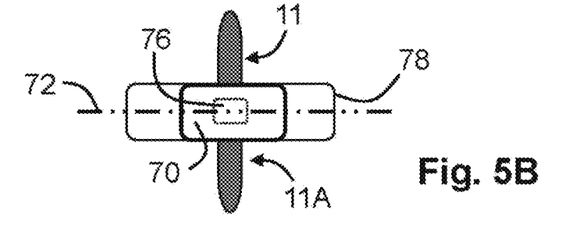
Figure 5C:
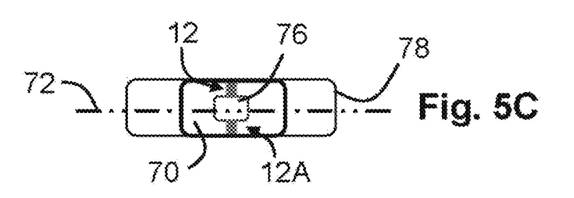
Figure 5D:
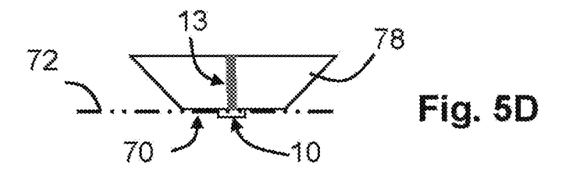
Figure 5E:
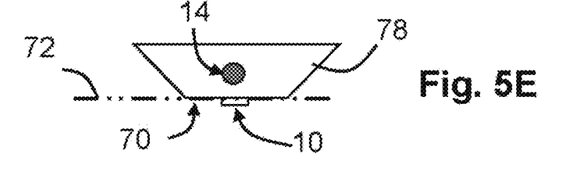

FIGS. 5A, 5B, 5C, 5D and 5E show different guidance elements 10, 11, 12, 13, 14 for indicating to a user the location in the emission window from which, in use, the laser light will be emitted from the emission window 70 during the line treatment mode. In all of the FIGS. 5A to 5E, an emission tip 78 is illustrated which interacts with the skin surface 105 and which is configured to be moved relative to the skin surface 105 such that the laser light 21 from the treatment laser 20 may generate the lesions 120 according to the predefined distribution. The emission tip 78 comprises the emission window 70 together with the treatment axis 72. In FIG. 5A, the emission tip 78 comprises a protruding part 10 as a guidance element 10 for indicating where, in use, the laser light will be emitted from the emission window 70 during the line treatment mode. Such a protruding part 10 may even act as a tangible guidance element 10 such that the user may feel at what location during the scanning across the skin surface laser light is being emitted during the line treatment mode. FIG. 5B, which shows the emission tip 78, as viewed in the direction of the emission window 70, illustrates a visible indicator 11 which may, for example, comprise an optical projection of a light spot 11 or even elongated light spot 11 on the skin surface 105 (not indicated) to mark the location of a single-laser emission area 76 from which the laser light is emitted from the emission window 70 during the line treatment mode. Alternatively, a similar visible indicator 11A may be optically projected on the skin surface 105 on an opposite side of the emission window 70 to allow a user to move the emission tip 78 of the treatment device 100 in opposite directions relative to the skin surface 105 while still indicating the position of the single-laser emission area 76. FIGS. 5C, 5D and 5E show similar visible indicators 12, 13, 14, which indicate the position of the laser emission location 76 in the emission window 70. These visible indicators 12, 13, 14 may, for example, be a projected light spot 12, 13, 14 of visible light projected on a part of the housing of the treatment device surrounding the emission window 70 to indicate the location of the laser emission. Alternatively, these visible indicators 12, 13, 14 may, for example, be light emitting indicators 12, 13, 14 such as a Light Emitting Diode 12, 13, 14 or may, for example, be a colored marker 12, 13, 14 applied on a part of the housing of the treatment device surrounding the emission window 70. Each of these visible indicators 12, 13, 14 may have a similar indicator 12A, 13A, 14A (13A and 14A are not indicated) applied on a part of the housing of the treatment device surrounding the emission window 70, on an opposite side of the emission window 70 compared to the visible indicators 12, 13, 14, similar to the arrangement shown in FIG. 5B. Of course, any combination of the guidance elements 10 to 14 shown above may be applied to indicate the laser emission from the emission window 70 during the line treatment mode.

Figure 6A:
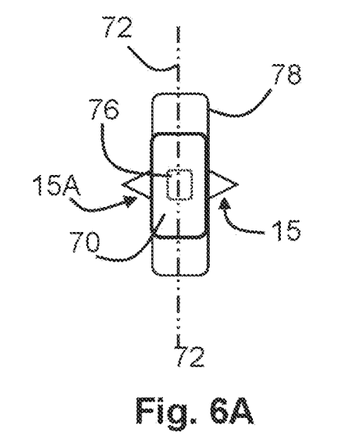
FIGS. 6A, 6B, 6C and 6D show different mechanical guidance elements.
Figure 6B:
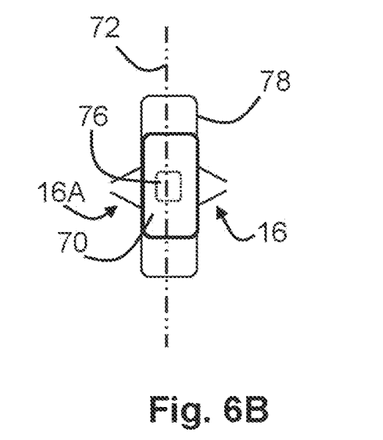
Figure 6C:
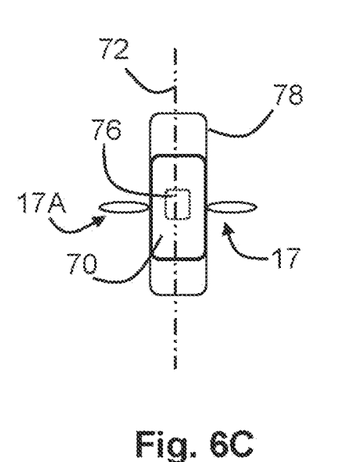

FIGS. 6A, 6B, 6C and 6D show different mechanical guidance elements 15, 16, 17, 18. FIGS. 6A to 6D show the emission tip 78, as viewed in the direction of the emission window 70 in which the laser emission location 76 in the line treatment mode is indicated. Also indicated is the treatment axis 72. In FIG. 6A, a mechanical guidance element 15 is shown which comprises an extension 15 protruding, in a direction parallel to the intended movement direction of the treatment device, from a part of the housing of the treatment device surrounding the emission window 70 to indicate the location of the laser emission location 76 in the line treatment mode. This mechanical guidance element 15 has a triangular shape to allow a user to follow a wrinkle or fine line, using the tip of the triangular shape to ensure that the laser emission location 76 passes over the wrinkle or fine line to ensure that this wrinkle or fine line is treated according to the line treatment process. To allow a user to move the emission tip 78 in opposite directions while still indicating the position of the laser emission location 76, a second similar mechanical guidance element 15A may be arranged protruding parallel to the intended movement direction of the treatment device from a part of the housing of the treatment device on the opposite side of the emission window 70 compared to the mechanical guidance element 15. FIG. 6C shows a different mechanical guidance element comprising a rolling element 17 which is attached to a part of the housing of the treatment device surrounding the emission window 70 and which is configured for rolling, in use, over the skin surface 105 for indicating the predefined location 76 in the emission window from which the laser light is emitted in the line treatment mode of the treatment device. Such a rolling element 17 may be a wheel, for example, rotating in a rotation plane perpendicular to the plane of the figure. The rolling element 17 is arranged such that its rolling plane substantially intersects with a center of the laser emission location 76 to identify the predefined location in the emission window from which the laser light is emitted. Again, a second similar rolling element 17A may be attached to a part of the housing of the treatment device surrounding the emission window, on the opposite side of the emission window to allow a user to move the emission tip 78 in opposite directions while still indicating the position of the laser emission location 76.

Figure 6D:
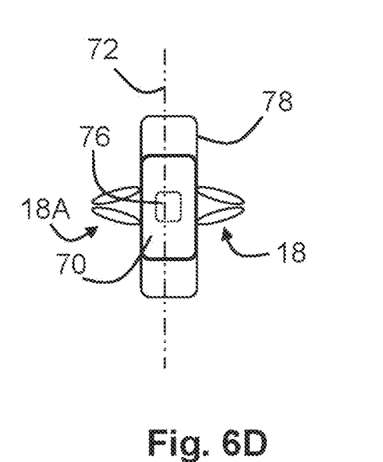

The embodiments of FIGS. 6B and 6D are similar to the embodiments of FIGS. 6A and 6C, respectively, wherein the embodiments of FIGS. 6B and 6D comprise mechanical guidance elements 16 and 18 which are additionally configured for leveling and/or stretching the skin surface 105 while the treatment device 100 moves relative to the skin surface 105. When using such mechanical guidance elements 16, 18 for leveling and/or stretching the skin surface 105 during the treatment, the contact of the treatment device 100 with the skin surface 105 is improved, thereby ensuring that the skin treatment is performed correctly. FIG. 6B shows two extensions 16 arranged adjacent each other, protruding from a part of the housing of the treatment device surrounding the emission window 70 and forming an opening between the two adjacent extensions 16. The two extensions are configured such that adjacent extensions 16 converge towards each other in a direction away from the emission window, causing the opening to converge in a direction away from the treatment device 100. Preferably, the opening between the two converting extensions 16 forms a kind of triangular opening in which the two adjacent extensions 16 do not touch to close the opening. Therefore, when the mechanical guidance element 16 slides across the skin surface 105, the opening at the top of the triangle guides the part of the skin which is to be treated towards the predefined location 76 in the emission window from which the laser light is emitted. Due to the triangular shape, the guided skin part will be stretched, which ensures good contact between the laser emission location 76 of the emission window 70 and the skin surface 105. FIG. 6D shows two rolling elements 18 arranged adjacent each other and configured for rolling, in use, over the skin surface 105, wherein an intermediate space between said two rolling elements converges in a direction away from the emission window 70. Also such adjacent rolling elements 18, which may also form a kind of a triangular arrangement, preferably do not touch, so that the triangular shape of the intermediate space on the side facing away from the emission window 70 is open to guide the part of the skin surface 105 which is to be treated towards the laser emission location 76 in the emission window. This triangular arrangement of the adjacent rolling elements 18 subsequently stretches the guided part of the skin surface 105 to ensure good contact between the laser emission location 76 of the emission window 70 and the skin surface 105. Each of these mechanical guidance elements 15, 16, 17, 18 may be combined with an identical mechanical guidance element 15A, 16A, 17A, 18A applied to the part of the housing of the treatment device situated on an opposite side of the emission window 70, similar to the arrangement shown in FIGS. 5B and 5C.

The treatment device according to the invention may alternatively comprise a laser scanning system of a different kind than the rotatable deflection wheel as described hereinbefore. In any embodiment of the invention, the laser scanning system comprises at least one movable deflection element which is maintained in a stationary position relative to the emission window in the line treatment mode of the treatment device. An example of a suitable alternative laser scanning system is a laser scanning system comprising at least one mirror which can be pivoted about a pivot axis located in a reflective surface of the mirror. One such mirror is needed to scan the laser light along the line of locations 74 in the emission window shown in FIG. 3A, and two such mirrors would be needed to scan the laser light along the array of locations 74 in the emission window shown in FIG. 3C.

In summary, the invention provides a treatment device 100 for fractional laser-based treatment. The treatment device comprises a treatment generator 80 comprising a treatment laser 20 and a laser scanning system 30. The laser scanning system comprises at least one movable deflection element and is configured and arranged for scanning laser light across an emission window 70 towards skin tissue 110 from a plurality of predefined locations 74 in the emission window by moving the at least one deflection element relative to the emission window, whereby, in use, laser-based lesions 120 are generated inside the skin tissue. The treatment device also comprises a controller 60 for generating a predefined disposition of lesions 120 in the skin tissue by emitting laser light via selected ones of the predefined locations while the treatment device is moving relative to the skin surface 105. The controller is configured for generating an area disposition of the lesions by scanning the laser light across the emission window using the laser scanning system and deflecting laser light into the skin tissue via the plurality of locations, while in the line treatment mode the controller is configured to generate a line disposition of the lesions inside the skin tissue from a single location of the emission window by maintaining the at least one deflection element in a stationary position relative to the emission window.

It will be appreciated that the invention—especially many of the method steps indicated above—also extends to computer programs, particularly computer programs on or in a carrier, adapted for putting the invention into practice. The program may be in the form of source code, object code, a code intermediate source and object code such as a partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or system capable of carrying the program. For example, the carrier may include a storage medium, such as a ROM, for example a CD ROM or a semiconductor ROM, or a magnetic recording medium, for example a floppy disc or hard disk. Further, the carrier may be a transmissible carrier such as an electrical or optical signal, which may be conveyed via electrical or optical cable or by radio or other means. When the program is embodied in such a signal, the carrier may be constituted by such an electrical or optical cable or other system or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the system claim enumerating several means, several of these means may be embodied by one and the same item of hardware. The mere fact that certain measures are recited in mutually different dependent claims does not indicate that a combination of these measures cannot be used to advantage.

The invention claimed is:

1. A treatment device for fractional laser-based skin treatment, the treatment device comprising:
    an emission window;
    a treatment generator that comprises (i) a treatment laser for emitting laser light and (ii) a laser scanning system, wherein the laser scanning system comprises at least one movable deflection element configured and arranged for scanning laser light across the emission window towards skin tissue from a plurality of locations in the emission window by moving the at least one deflection element relative to the emission window, whereby, in use, laser-based lesions are generated inside the skin tissue; and
    a controller configured for generating a predefined disposition of the lesions in the skin tissue by emitting laser light via selected ones of the locations of the plurality of locations while the treatment device, in use, is moved relative to the skin surface,
    wherein the controller is configured for operating alternatively (i) in an area treatment mode and (ii) in a line treatment mode, different from the area treatment mode, and
    wherein, in the area treatment mode, the controller is configured for generating an area disposition of the lesions inside the skin tissue by moving the at least one deflection element relative to the emission window while the treatment device, in use, is moved relative to the skin surface, and
    wherein, in the line treatment mode, the controller is configured to generate a line disposition of the lesions inside the skin tissue by maintaining the at least one movable deflection element of the laser scanning system in a stationary position relative to the emission window, via preventing a movement of the at least one movable deflection element, such that the laser light is emitted from the emission window from only a single predefined fixed location of the plurality of locations during the line treatment mode, while the treatment device, in use, is moved relative to the skin surface.

2. The treatment device according to claim 1, wherein the laser scanning system comprises a rotatable deflection wheel having a plurality of deflection elements being configured for deflecting the laser light, during rotation of the deflection wheel, sequentially towards individual ones of the plurality of locations in the emission window.

3. The treatment device according to claim 2, wherein the deflection wheel is an axicon deflection wheel.

4. The treatment device according to claim 2, wherein, in the line treatment mode, the controller is configured for generating the line disposition of the lesions inside the skin tissue by maintaining the rotatable deflection wheel in a stationary angular position relative to the emission window.

5. The treatment device according to claim 4, wherein the deflection wheel, in the line treatment mode, is maintained in the stationary angular position relative to the emission window by means of a blocking mechanism.

6. The treatment device according to claim 5, wherein the blocking mechanism is selected from the list comprising:
    a mechanical blocking element for mechanically preventing the deflection wheel from rotating, or
    a magnetic blocking element for magnetically preventing the deflection wheel from rotating, or
    an electrical blocking mechanism for interrupting a supply of power to a motor configured for rotating the deflection wheel.

7. The treatment device according to claim 5, wherein the blocking mechanism is configured for blocking the deflection wheel in a predefined stationary angular position relative to the emission window wherein the laser light is deflected towards a predefined one of the plurality of locations in the emission window.

8. The treatment device according to claim 5, wherein the blocking mechanism, when maintaining the deflection wheel in the stationary angular position relative to the emission window, generates a signal indicating to the controller that the deflection wheel is in a blocked condition.

9. The treatment device according to claim 1, wherein the treatment device comprises a guidance element for indicating to a user a predefined location in the emission window from which, in the line treatment mode, the laser light is emitted towards the skin tissue.

10. The treatment device according to claim 9, wherein the guidance element comprises a protruding part protruding from a part of a housing of the treatment device surrounding the emission window.

11. The treatment device according to claim 9, wherein the guidance element comprises a visible indicator selected from a list comprising: an optical projection of an indicator on the skin surface near the emission window using visible light, an optical projection of an indicator on a part of a housing of the treatment device surrounding the emission window using visible light, a light emitting indicator attached to the treatment device near the emission window, and a colored marker applied on a part of a housing of the treatment device surrounding the emission window.

12. The treatment device according to claim 9, wherein the treatment device has an intended movement direction in which, at least in the line treatment mode, the treatment device is to be moved relative to the skin surface, and wherein the guidance element comprises a mechanical guidance element comprising:
    an extension protruding parallel to the intended movement direction from a part of a housing of the treatment device surrounding the emission window, or
    a rolling element attached to a part of a housing of the treatment device surrounding the emission window and configured for rolling, in use, over the skin surface.

13. The treatment device according to claim 9, wherein the guidance element comprises a mechanical guidance element comprising:
    two extensions arranged adjacent each other and configured for, in use, contacting the skin surface, said two extensions protruding from a part of a housing of the treatment device surrounding the emission window and converging towards each other in a direction away from the emission window, or
    two rolling elements arranged adjacent each other and configured for, in use, rolling over the skin surface, wherein an intermediate space between said two rolling elements converges in a direction away from the emission window.

14. The treatment device according to claim 1, wherein the treatment device is a handheld treatment device.

* * * * *